us006095326A

United States Patent [19]
Madhat et al.

[11] Patent Number: 6,095,326
[45] Date of Patent: Aug. 1, 2000

[54] PACKAGING OF DISPOSABLE GLOVES WITH CONSUMER TISSUE PRODUCTS

[76] Inventors: Maher N. Madhat, 3305 Grasmere Dr., Lexington, Ky. 40503; Munir A. Hussain, 619 Andover Rd., Wilmington, Del. 19803

[21] Appl. No.: 09/337,721

[22] Filed: Jun. 21, 1999

[51] Int. Cl.[7] .................................................. B65D 71/00
[52] U.S. Cl. ........................................... 206/233; 206/494
[58] Field of Search .................................. 206/570, 233, 206/494, 278, 440, 216

[56] References Cited

U.S. PATENT DOCUMENTS

| | | |
|---|---|---|
| D. 372,386 | 8/1996 | Kuchenbecker . |
| D. 372,387 | 8/1996 | Kuchenbecker . |
| 4,574,952 | 3/1986 | Masui . |
| 4,917,238 | 4/1990 | Schumacher ................... 206/570 X |
| 5,207,303 | 5/1993 | Oswalt et al. ................... 206/570 X |
| 5,259,550 | 11/1993 | Kuchenbecker . |
| 5,287,960 | 2/1994 | Kalb et al. . |
| 5,316,177 | 5/1994 | Boldt . |
| 5,415,320 | 5/1995 | North et al. . |
| 5,715,841 | 2/1998 | Utecht . |
| 5,718,245 | 2/1998 | Horn . |
| 5,867,832 | 2/1999 | Liu . |

*Primary Examiner*—Jacob K. Ackun

[57] ABSTRACT

Packaging of disposable gloves with consumer tissue products in order: To provide first aid protection (disposable gloves) in every type of package of consumer tissue products, and To utilize the widely used consumer tissue products as a vehicle to deliver the disposable gloves to end user. A new package form for consumer tissue products and particularly facial tissue for containing infectious body fluids resulting from the said injuries comprising: a) Any form of consumer package tissue products, b) One or more protective disposable gloves, c) Said gloves package having dimensions allowing said package to be incorporated in any existing forms and shapes of consumer tissue products and particularly facial tissue.

2 Claims, 1 Drawing Sheet

PACKAGING OF DISPOSABLE GLOVES WITH CONSUMER TISSUE PRODUCTS

BACKGROUND OF THE INVENTION

This invention relates generally to the field of containment of infectious body fluids, and more particularly to packaging of disposable gloves with consumer tissue products.

The danger of infection from AIDS and other diseases which are transmitted by contact with body fluids are well known. It is a common practice for medical personnel and other treating open wounds in the human body to wear gloves and other protective devices. Protective measures are necessary because a person requiring treatment may unknowingly be a carrier of viruses such as the human immunodeficiency virus (HIV). In some instances the victim of an accident may be unconscious and unable to warn others of possible hazards of infection. It has been shown that barrier type product such as protective gloves provide protection especially in case of emergency rescues and on site first aid treatment where the increased risks of contamination are likely the greatest. Rubber gloves (latex or vinyl) are the most functional and widely used of current protection devices and typically remains with care givers.

Many forms of personal protection devices and first aid packages were disclosed in order to provide a consumer products that can be used to contain contamination of body fluids (Leo Utech U.S. Pat. No. 5,715,841; Rodney Horn U.S. Pat. No. 5,718,245; Fang Liu U.S. Pat. No. 5,867,832; Irvine Kalb U.S. Pat. No. 5,287,960).

Consumer tissue products (facial tissues, bathroom tissues, and paper towels) and particularly facial tissues are available in every house, office, school, vehicles, plants and like. Therefore an opportunity exists to package with these products a pair or more of disposable gloves to be used in order to minimize or eliminate the contact with body fluids. Such inclusion of gloves with already widely available consumer tissue products will enhance their marketability and provide a significantly valued products at a minimum cost.

Inclusion of disposable gloves with the highly used consumer tissue products make both products conveniently and readily available within reach when needed. The use of tissue box is known in the prior art. More specifically, tissue box heretofore devised and utilized are known to consist basically of familiar, expected and obvious structural configurations, not withstanding the myriad of designs encompassed by the crowded prior art which have been developed for the fulfillment of countless objectives and requirements.

Known prior art tissue boxes include Morris Kuchenbecker U.S. Pat. Nos. design 372,387; 372, and U.S. Pat. No. 386; 5,259,550; North et al U.S. Pat. No. 5,415,320; Hans Boldt U.S. Pat. No. 5,316,177; Toshimune Masui U.S. Pat. No. 4,574,952. While these designs fulfill their respective, particular objectives and requirements, the aforementioned patents do not disclose a new facial tissue-glove combination box. The inventive design includes a tissue box having a pair or more of disposable gloves either outside or inside the box.

No one has developed a simple, attractive, readily accessible protective gloves with any consumer tissue products box for a variety of use. That is to provide a pair or more of disposable gloves along with widely used consumer tissue products. In these respects, the consumer tissue products and particularly facial tissue-glove box design according to the present invention substantially departs from the conventional concepts and design of prior art, and in so doing provides an apparatus primarily developed for the purpose of providing disposable protective gloves along with any type of consumer tissue products and facial tissue in particular.

SUMMARY OF THE INVENTION

First object of the invention is to provide protection to care giver to minimize the exposure to an infected individual.

Another object of the invention is first aid protection mainly disposable gloves to prevent exposure to body fluids.

Yet another object is to take advantage of the widely marketed consumer tissue products and facial tissue in particular.

Other objects and advantages of the present invention will become apparent from the following descriptions, taken in connection with the accompanying drawings, wherein, by way of illustration and example, an embodiment of the present invention is disclosed.

The present invention relates generally to personal protection that may be placed over the hand of the user in dealing with potentially infectious blood and body fluids. More particularly the invention concerns a barrier type protection for use in effectively treating trauma victims and patients having infectious diseases, bacteria, microorganisms, viruses, spores and blood born pathogens.

The present invention provides a novel protection tool that effectively protects personnel from exposure to bio hazardous materials of the character often encountered during emergency medical attention and cleanup situations. More particularly, the invention provides protective gloves packaged along with consumer tissue products and facial tissues in particular.

The invention provides first aid protection that permits quick and easy access to rubber gloves.

The invention provides personal protection of the movement of dangerous or undesirable fluids, viruses, spores, bacteria, microorganisms and other materials during first aid treatment at home, business, car, plants, and like.

The invention provides protective gloves in order to limit or deny passage of selected pathogens between persons or objects where prevention of cross. contamination is desirable.

The invention provides an inexpensive protective device to avoid a direct contact with body fluids.

In view of the foregoing advantages inherent in the known types of tissue box now present in the prior art, the present invention provides a new package by including a protective disposable gloves.

The general purpose of the present invention is to provide a new facial tissue-glove box which has many of the advantages of tissue box exist in the market heretofore and many novel feature that result in a new facial tissue box which is not anticipated, rendered obvious, suggested or even implied by any of the prior art of tissue box, either alone or in any combination thereof.

To attain this, the present invention generally comprises a tissue dispensing box having a pocket (inside or outside) to house a pair or more of disposable gloves It is an object of the present invention to provide a new facial tissue-glove box which has many advantages over tissue alone which is not anticipated, rendered obvious, suggested, or even implied by any of the prior art tissue boxes. It is another object of the present invention to provide a new facial tissue-glove box which may be easily and efficiently manufactured and marketed.

An even further object of the present invention is to provide a new facial tissue-glove box which is susceptible of low prices of sale to the consuming public, thereby making such facial tissue-glove box economically available to the buying public.

Still another object of the present invention is to provide a new facial tissue-glove box that reduces the cost of buying each product separately and thus limiting the need to purchase the glove box.

The present invention is directed to a factory of consumer tissue products and facial tissue in particular in which a protective glove is included. The glove is molded outside the box and form an integral part of the box.

In a preferred embodiment, the glove is located in a readily accessible location on the box.

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Figure 2:
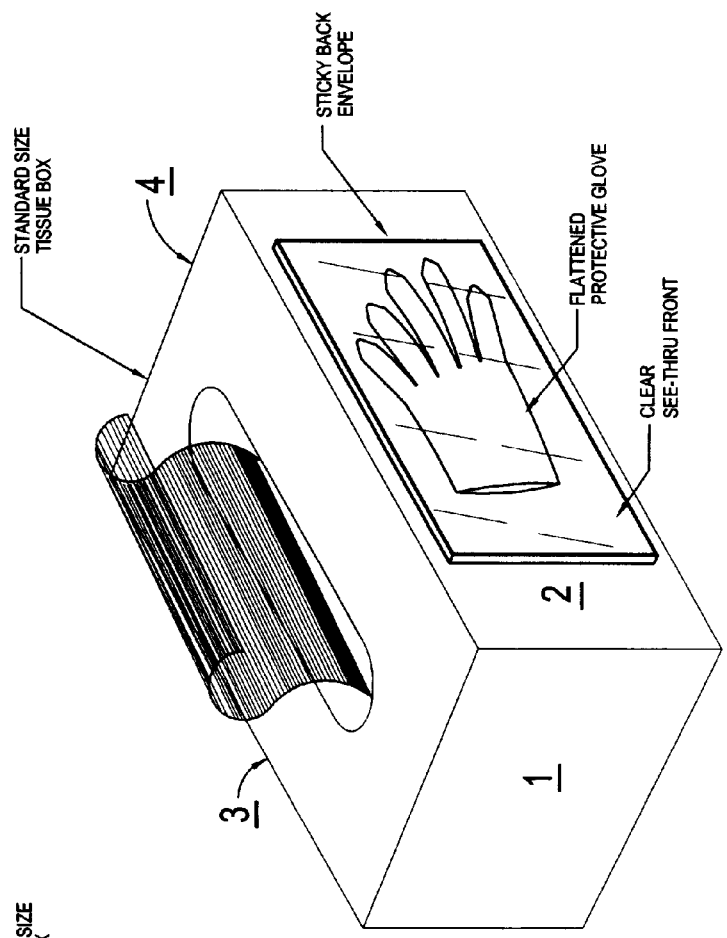
FIG. 2 is a perspective view of a tissue carton of this invention, illustrating a set of glove(s) that can be placed at any side (1–4)
Figure 1:
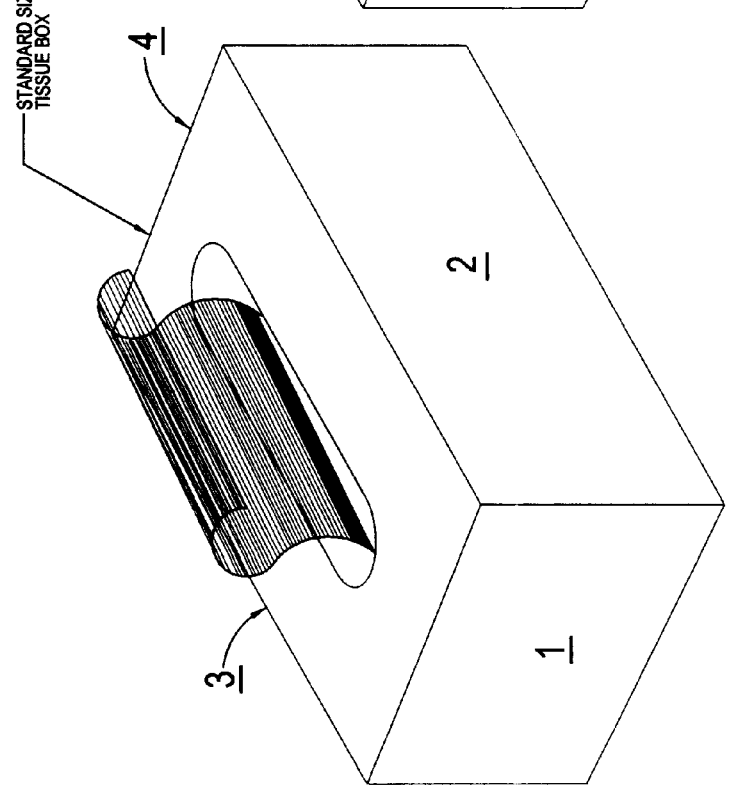
FIG. 1 is a perspective view of a prior art of facial tissue carton, illustrating a slit plastic film dispensing window.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

The invention comprises material for treating an open wound packaged in any form of consumer tissue products and facial tissues in particular. The method may include the steps of a. Placing one or more disposable gloves in every type, shapes or forms of consumer tissue products and particularly facial tissue b. Removing the glove by care giver c. It is to be understood that a number of different kinds of containers may be used to package the protective gloves including boxes, tubes, vial, foil and like construction d. While the protective gloves addition to all consumer tissue products packages and particularly facial tissue may be used for various purposes including wound treatment and also contamination clean up and like purposes.

The embodiments described above are only exemplary. We do not claim to have invented all the elements involved.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A package comprising a box having facial tissues therein, the box having means thereon to facilitate dispensing said facial tissues therefrom, an envelope adhesively attached to a wall of said box, said envelope containing a flattened pair of disposable gloves therein, said envelope further comprising a transparent wall to facilitate viewing of said gloves.

2. The package of claim 1, wherein said envelope is constructed of plastic and is attached to said box on an inside or outside surface thereof.

* * * * *